United States Patent
Rusher

(10) Patent No.: US 11,452,838 B2
(45) Date of Patent: Sep. 27, 2022

(54) POSITIVE EXPIRATORY PRESSURE DEVICES WITH FLUTTER VALVE

(71) Applicant: Michael J. Rusher, Ft. Wayne, IN (US)

(72) Inventor: Michael J. Rusher, Ft. Wayne, IN (US)

(*) Notice: Subject to any disclaimer, the term of this patent is extended or adjusted under 35 U.S.C. 154(b) by 410 days.

(21) Appl. No.: 16/693,915

(22) Filed: Nov. 25, 2019

(65) Prior Publication Data
US 2020/0086074 A1    Mar. 19, 2020

Related U.S. Application Data

(63) Continuation-in-part of application No. 15/412,432, filed on Jan. 23, 2017, now abandoned, which is a
(Continued)

(51) Int. Cl.
*A61M 16/20*      (2006.01)
*A61M 16/08*      (2006.01)
(Continued)

(52) U.S. Cl.
CPC ...... *A61M 16/208* (2013.01); *A61M 16/0006* (2014.02); *A61M 16/0833* (2014.02);
(Continued)

(58) Field of Classification Search
CPC .......... A61M 16/0006; A61M 16/0866; A61M 16/208; A63B 23/18
See application file for complete search history.

(56) References Cited

U.S. PATENT DOCUMENTS 3,291,127 A    12/1966    Elmer et al.
3,511,228 A    5/1970    Lundgren et al.
(Continued)

FOREIGN PATENT DOCUMENTS

CA    2 808 043    9/2013
CN    101219249 A    7/2008
(Continued)

OTHER PUBLICATIONS

Machine Translation of FR 2884724.
(Continued)

*Primary Examiner* — Joseph D. Boecker
(74) *Attorney, Agent, or Firm* — Woodard, Emhardt, Henry, Reeves & Wagner, LLP

(57) ABSTRACT

A positive pressure airway device for providing resistance in an air pathway for a patient exhaling. The device includes a central tube region, a inspiratory air passageway for passing air into the central tube region when a patient breathing through the device inhales, and an expiratory air passageway for passing air out of the central tube region when a patient breathing through the device exhales, A valve in the expiratory air passageway allows air to flow out only when a patient using the device exhales with an expiratory air pressure greater than a selected pressure, and includes a stopper and a coil spring with an interior portion that is free from any structure that would inhibit the "side-to-side" movement of the spring within the housing. The stopper has a cone-shaped air-stopping surface providing a valve angle that is different from the valve-seat angle so that either laminar or oscillating flow may be obtained.

15 Claims, 12 Drawing Sheets

Related U.S. Application Data continuation-in-part of application No. 14/175,385, filed on Feb. 7, 2014, now abandoned, which is a continuation-in-part of application No. 13/459,564, filed on Apr. 30, 2012, now abandoned.

(60) Provisional application No. 61/761,938, filed on Feb. 7, 2013, provisional application No. 61/480,097, filed on Apr. 28, 2011.

(51) Int. Cl.
*A61M 16/00* (2006.01)
*A63B 23/18* (2006.01)

(52) U.S. Cl.
CPC ...... *A61M 16/0866* (2014.02); *A61M 16/201* (2014.02); *A63B 23/18* (2013.01); *A61M 2202/0208* (2013.01); *A61M 2205/3331* (2013.01)

(56) References Cited

U.S. PATENT DOCUMENTS

| | | |
|---|---|---|
| 3,933,171 A | 1/1976 | Hay |
| 4,207,884 A | 6/1980 | Isaacson |
| 4,221,381 A | 9/1980 | Ericson |
| 4,316,458 A | 2/1982 | Hammerton-Fraser |
| 4,854,574 A | 8/1989 | Larson et al. |
| 5,301,667 A | 4/1994 | Mc Grail et al. |
| 5,425,358 A | 6/1995 | McGrail et al. |
| 5,598,839 A | 2/1997 | Niles et al. |
| 5,871,011 A | 2/1999 | Howell et al. |
| 6,102,038 A | 8/2000 | DeVries |
| 6,581,598 B1 | 6/2003 | Foran et al. |
| 6,679,250 B2 | 1/2004 | Walker et al. |
| 6,726,598 B1 * | 4/2004 | Jarvis ................. A63B 23/18 128/200.24 |
| 6,792,947 B1 | 9/2004 | Bowden |
| 7,134,434 B2 | 11/2006 | Truitt et al. |
| 7,699,054 B2 | 4/2010 | Pelerossi et al. |
| 7,735,492 B2 | 6/2010 | Doshi et al. |
| 8,025,054 B2 | 9/2011 | Dunsmore et al. |
| 8,225,785 B2 | 7/2012 | Richards et al. |
| 8,327,849 B2 | 12/2012 | Foley et al. |
| 9,233,274 B2 | 1/2016 | Lau |
| 2002/0134384 A1 | 9/2002 | Bienvenu et al. |
| 2003/0140925 A1 | 7/2003 | Sapienza et al. |
| 2003/0234017 A1 | 12/2003 | Pelerossi et al. |
| 2009/0032619 A1 | 2/2009 | Morgan et al. |
| 2010/0101573 A1 | 4/2010 | Foley et al. |
| 2010/0282262 A1 | 11/2010 | Boussignac |
| 2012/0204887 A1 | 8/2012 | Connor |
| 2012/0272956 A1 * | 11/2012 | Rusher ................. A63B 23/18 128/203.12 |
| 2014/0150801 A1 * | 6/2014 | Rusher ............... A63B 21/0088 128/207.16 |
| 2017/0136205 A1 * | 5/2017 | Rusher ................. A63B 23/18 |

FOREIGN PATENT DOCUMENTS

| | | |
|---|---|---|
| DE | 102007062861 A1 | 6/2009 |
| EP | 0 678 306 B1 | 11/2001 |
| EP | 1 435 251 B1 | 6/2006 |
| EP | 1 103 287 B1 | 6/2007 |
| EP | 1 464 357 B1 | 1/2010 |
| EP | 2 444 114 A1 | 4/2012 |
| EP | 2 636 420 A1 | 9/2013 |
| FR | 2 884 724 A1 | 10/2006 |
| WO | WO 2013/096988 A1 | 7/2013 |

OTHER PUBLICATIONS

Machine Translation of De 102007062861.
English Abstract of CN101219249A.
Search Report for PCT/US2020/062193, dated Mar. 17, 2021.
Written Opinion for PCT/US2020/062193, dated Mar. 17, 2021.

* cited by examiner

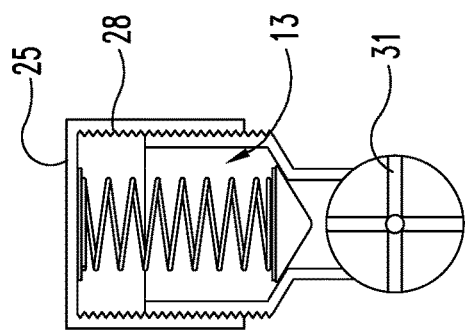
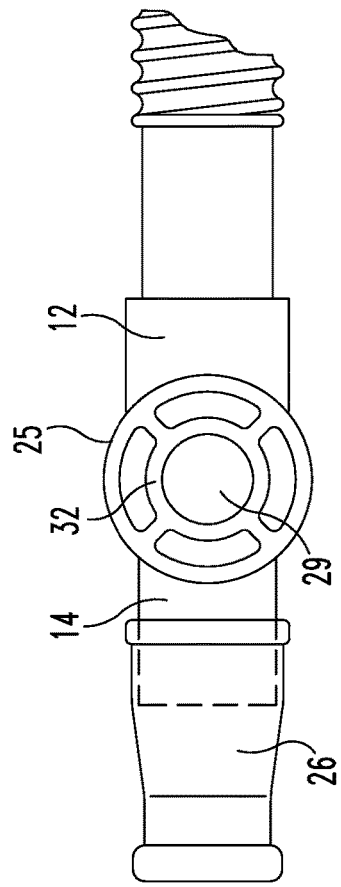
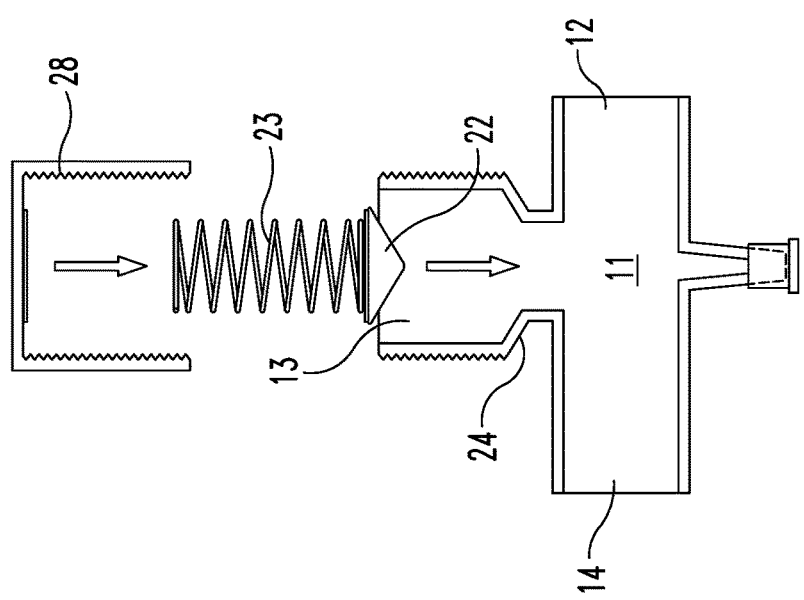

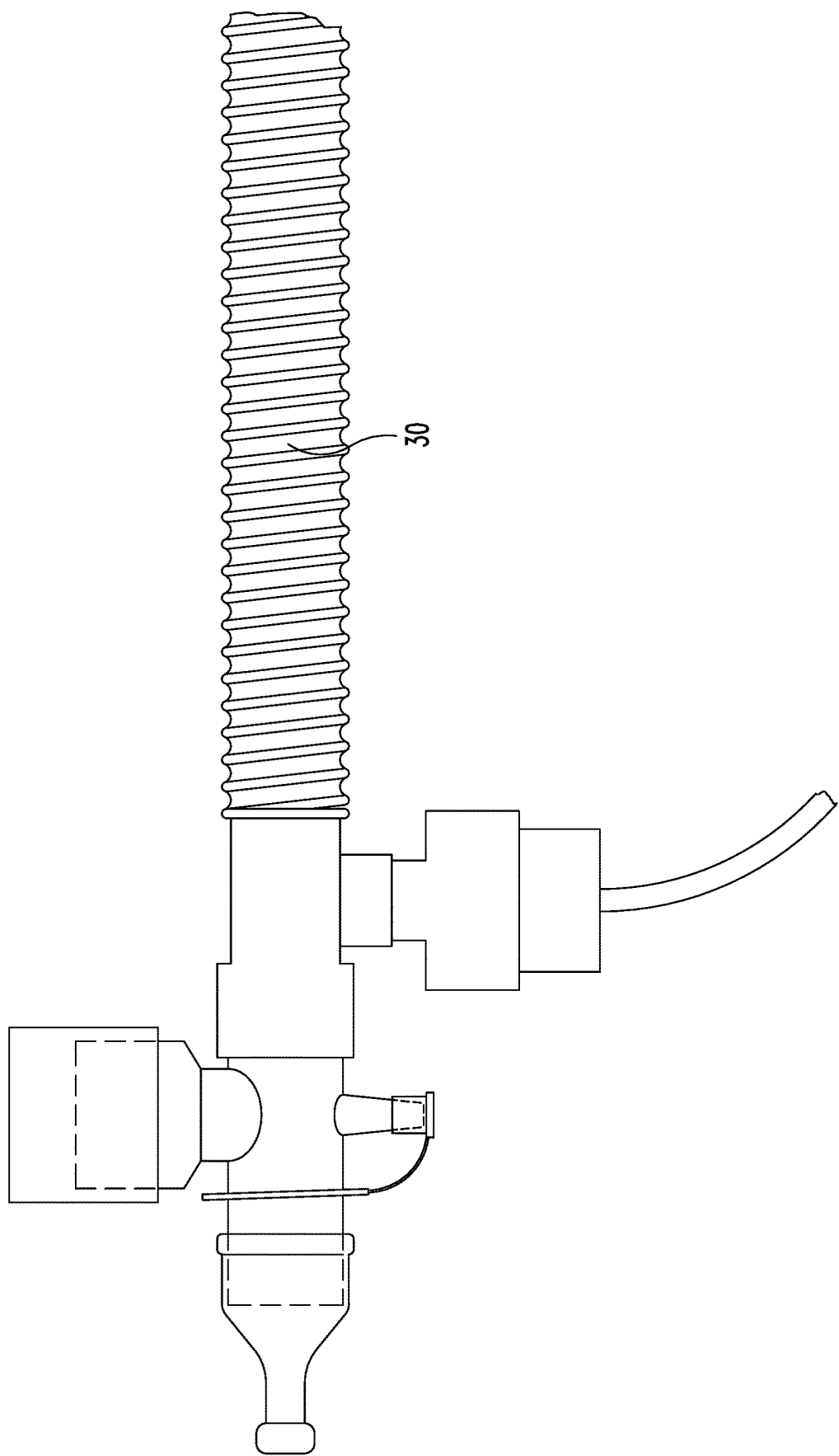

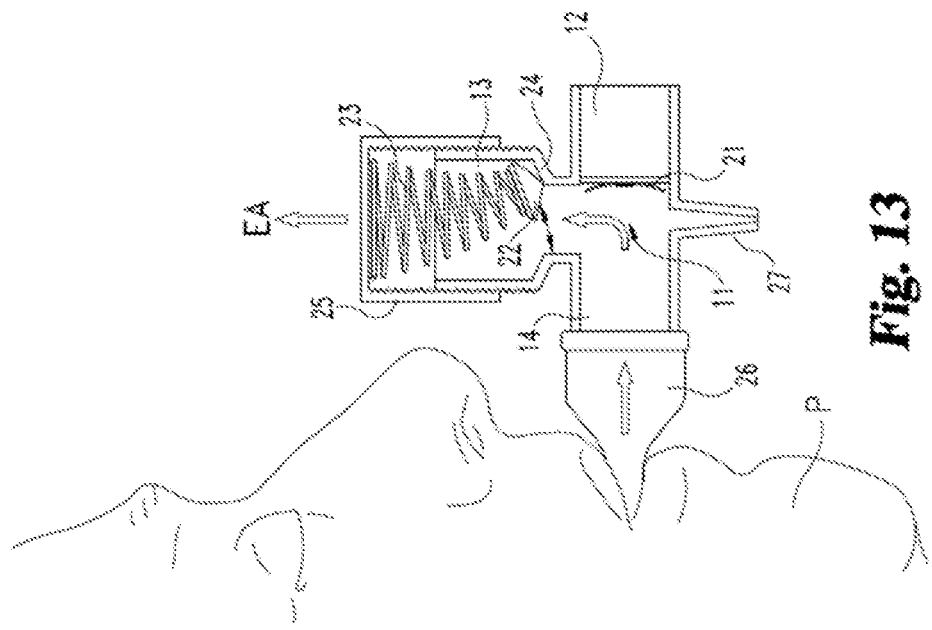
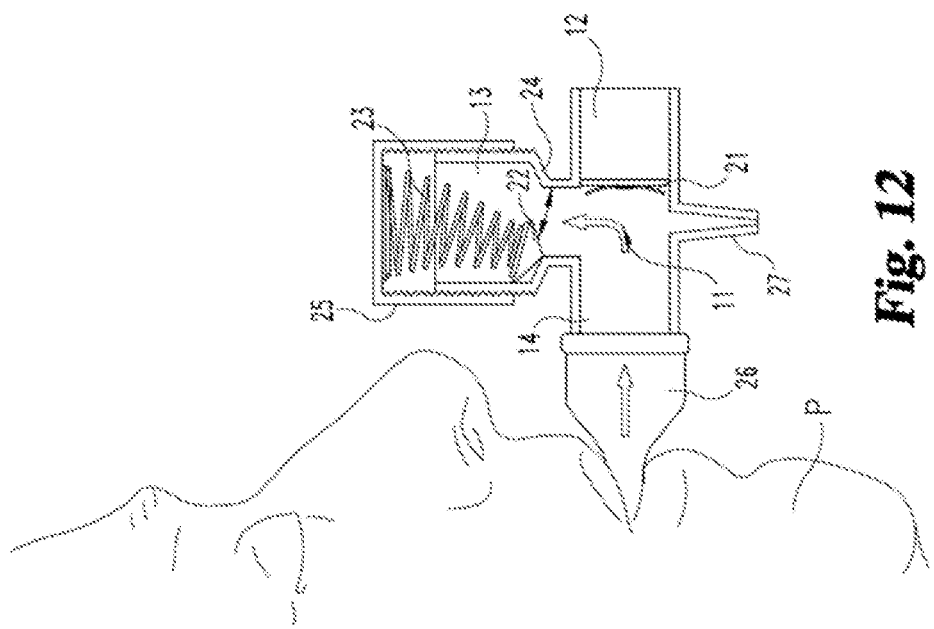

POSITIVE EXPIRATORY PRESSURE DEVICES WITH FLUTTER VALVE

REFERENCE TO RELATED APPLICATIONS

This application claims the benefit of U.S. patent application Ser. No. 15/412,432, filed Jan. 23, 2017, which claims the benefit of U.S. patent application Ser. No. 14/175,385, filed Feb. 7, 2014, which claims the benefit of U.S. Provisional Patent Application Ser. No. 61/761,938, filed Feb. 7, 2013, and of U.S. patent application Ser. No. 13/459,564, filed Apr. 30, 2012, and of U.S. Provisional Patent Application Ser. No. 61/480,097, filed Apr. 28, 2011. The entire contents of each of the foregoing is incorporated into this application by reference.

FIELD OF THE INVENTION

This application relates generally to airway pressure control devices, and more particularly to a positive expiratory pressure device with an oscillating pressure valve to control expiratory air flow.

BACKGROUND

Patients that have compromised lungs due to decreased lung capacity resulting from COPD (Chronic Obstructive Pulmonary Disease), CHF (Congestive Heart Failure), or Pulmonary Edema, atelectasis, and/or decreased lung capacity due to pain or inhibited abdominal diaphragm function, may benefit from therapy such as positive expiratory pressure (PEP) therapy. Patients in need of PEP therapy may not generally exhale with enough force to expand the alveoli. For example, pressures within the alveoli typically range from 4 $cmH_2O$ to 6 $cmH_2O$, and when pulmonary capillary pressures (normal range 3 $cmH_2O$) exceed the alveoli pressures, blood seeps into the alveoli. In this situation it is critical to add pressure greater than 6 $cmH_2O$ to the space within the alveoli.

Devices that increase expiratory air pressure are known. For example, positive expiratory pressure (PEP) devices are typically small devices that a patient exhales into, optionally using a mask. The PEP device creates pressure in the lungs and keeps the airways from closing. The air flowing through the PEP device helps move the mucus into the larger airway. However, known prior art devices use strictures or small orifices to produce positive expiratory pressures. This may compromise flow with increased friction, requiring more work to exhale. Additionally, some known PEP devices are useful only for allowing a patient to exhale, and may not be used for normal in-and-out breathing.

It is also known that medical ventilators mechanically move breathable air into and out of the lungs, and assist patients who need help breathing or are physically unable to breathe. Such ventilators may pump regular air or oxygen-enriched air to a patient, and are typically connected to a patient's lungs through two tubes through which air may flow: an inspiration tube to provide air/oxygen to the patient's lungs; and an expiration tube to receive exhaled air back from the patient. The inspiration pathway provides air/oxygen that is pumped by the ventilator at a pressure of between 5 and 25 cm of water pressure, depending on the patient's needs. The expiration pathway is passive.

The flow of air (which may be regular, atmospheric air or oxygen-enriched air or some other gas, as desired by medical personnel, all of which will be referred to generically as "air" in this disclosure) is typically controlled by one of two methods. In one method the flow of air is provided under a "pressure control" system in which the flow is provided until it faces a set pressure as detected by a pressure sensor. In the other method the flow of air is provided under a "volume control" system in which the flow is provided until a predetermined volume of air has been delivered. In both cases, the ventilator delivers air at a breath rate (in breaths per minute) that is also set by the ventilator operator.

In some cases a problem may arise if the pressure in the inspiratory tube rises above a level that is safe for the patient. This is particularly a problem when the ventilator is operating in a volume control mode, although excessive pressure may arise even when the ventilator is operating in a pressure control mode.

A need therefore exists for devices that can increase patient safety by providing a positive pressure for expiratory air and/or by preventing the pressure in the inspiratory tube of a medical ventilator from reaching a level that is unsafe for the patient. The present invention addresses those needs.

SUMMARY OF THE INVENTION

Briefly describing one aspect of the present invention, there is provided a positive pressure airway device for providing resistance in an air pathway for a patient exhaling. In one embodiment the positive pressure airway device comprises or consists essentially of:

a) a central tube region;

b) a first passageway for passing air into the central tube region when a patient breathing through the device inhales;

c) a second passageway for passing air out of the central tube region when a patient breathing through the device exhales, wherein the second passageway has an upper portion defined by upper wall, a lower portion defined by a lower wall, and a transitional wall connecting the lower wall to the upper wall, and wherein the transitional wall is slanted at an angle α with respect to a line perpendicular to the vertical axis of the second passageway, thus providing a passageway having a valve seat angle α;

d) a third passageway for passing air from the central tube region and into a patient when the patient breathing through the device inhales, and for passing air from the patient to the central tube when the patient breathing through the device exhales;

e) a valve in the first passageway that allows air to flow in through the first passageway to the central tube when a patient using the device inhales, and that prevents air from flowing out through the first passageway when a patient using the device exhales;

f) a valve in the second passageway that allows air to flow out from the second passageway when a patient using the device exhales with an expiratory air pressure greater than a selected pressure, that prevents air from flowing out through the second passageway when a patient exhales with an expiratory air pressure that is less than said selected air pressure, and that prevents air from flowing in through the second passageway when a patient using the device inhales, wherein the valve in said second passageway includes:

i) a stopper to close the passageway and to prevent air from flowing through the passageway when the stopper is biased to its closed position, and ii) a stopper-biasing spring to maintain the stopper in a fixed and closed position unless the expiratory air pressure in the passageway is greater than a selected pressure, wherein the stopper-biasing spring is a coil spring having a stopper end connected to the stopper, and a cap end opposite the stopper end and connected to a spring housing cap; and g) a spring housing cap to retain the stopper-biasing spring and to partially compress the spring to a length shorter than its free length, wherein the spring housing cap is movable with respect to the transitional portion of the second passageway wall so that movement of the spring housing is effective for varying the compression length of the spring, and thus is effective for varying the expiratory air pressure that will cause the valve to open, and wherein the stopper-biasing spring is attached at its cap end to the spring housing cap, and at its stopper end to the stopper, with the center (interior) of the spring being free from any structure that would inhibit the "side-to-side" movement of the spring within the housing;

wherein the stopper has an exterior surface defining a plug angle β with respect to a line perpendicular to the vertical axis of the plug.

In some embodiments the valve seat angle α is greater than plug angle β, and the stopper-biasing spring tapers inward from its cap end to its stopper end, thus facilitating an oscillating movement of the plug in the passageway.

In other embodiments the valve seat angle α is less than or equal to plug angle β, and the spring tapers outward from its cap end to its stopper end, thus facilitating a laminar movement of the plug in the passageway.

In some embodiments the valve-seat angle is between 20° and 30° and the valve stopper angle is between 15° and 25°. In some embodiments the valve-seat angle is approximately 25° and the valve plug angle is approximately 20°.

In some embodiments the stopper is made of a first material having a first weight per unit volume, and includes a weighted portion made of a second material having a weight per unit volume that is greater than said first weight per unit volume. The weighted portion may be positioned below the region at which the stopper contacts the second passageway when sealing the second passageway from air flow.

In other embodiments there is provided a method for requiring a patient to breathe out with a pre-determined expiratory air pressure. The method comprises or consists essentially of:

a) providing a device for providing resistance in an air pathway for the patient exhaling, the device comprising:

1) a central tube region;

2) a first passageway for passing air into the central tube region when a patient breathing through the device inhales;

3) a second passageway for passing air out of the central tube region when a patient breathing through the device exhales, wherein the second passageway has an upper portion defined by upper wall, a lower portion defined by a lower wall, and a transitional wall connecting the lower wall to the upper wall, and wherein the transitional wall is slanted at an angle α with respect to a line perpendicular to the vertical axis of the second passageway, thus providing a passageway having a valve seat angle α;

4) a third passageway for passing air from the central tube region and into a patient when the patient breathing through the device inhales, and for passing air from the patient to the central tube when the patient breathing through the device exhales;

5) a valve in the first passageway that allows air to flow in through the first passageway to the central tube when a patient using the device inhales, and that prevents air from flowing out through the first passageway when a patient using the device exhales;

6) a valve in the second passageway that allows air to flow out from the second passageway when a patient using the device exhales with an expiratory air pressure greater than a selected pressure, that prevents air from flowing out through the second passageway when a patient exhales with an expiratory air pressure that is less than said selected air pressure, and that prevents air from flowing in through the second passageway when a patient using the device inhales, wherein the valve in said second passageway includes:

i) a stopper to close the passageway and to prevent air from flowing through the passageway when the stopper is biased to its closed position, and ii) a stopper-biasing spring to maintain the stopper in a fixed and closed position unless the expiratory air pressure in the passageway is greater than a selected pressure, wherein the stopper-biasing spring is a coil spring having a stopper end connected to the stopper, and a cap end opposite the stopper end and connected to a spring housing cap; and 7) a spring housing cap to retain the stopper-biasing spring and to partially compress the spring to a length shorter than its free length, wherein the spring housing cap is movable with respect to the transitional portion of the second passageway wall so that movement of the spring housing is effective for varying the compression length of the spring, and thus is effective for varying the expiratory air pressure that will cause the valve to open, and wherein the stopper-biasing spring is attached at its cap end to the spring housing cap, and at its stopper end to the stopper, with the center (interior) of the spring being free from any structure that would inhibit the "side-to-side" movement of the spring within the housing;

wherein the stopper has an exterior surface defining a plug angle β with respect to a line perpendicular to the vertical axis of the plug; and b) breathing out through said device with sufficient expiratory air pressure to cause said expiratory air valve to open, allowing air to exit the device.

BRIEF DESCRIPTION OF THE DRAWINGS

FIG. 3 shows an exploded section view of the device of FIGS. 1 and 2.

FIG. 4 shows an end view the device of FIGS. 1 and 2, showing the opening of the inhalation tube and the valve support therein.

FIG. 5 shows a top plan view the device of FIGS. 1 and 2, showing the opening of the exhalation tube and the spring-retaining housing thereon.

FIG. 6 shows a side view the device of FIGS. 1 and 2, with a nebulizer attached to the inhalation opening.

FIG. 12 shows a side view, in partial section, of one aspect of the present invention, particularly showing a device according to FIG. 1 but with a tapered spring and a rounded valve seat, as the illustrated device is being used to inhale.

FIG. 13 shows a side view, in partial section, of the device of FIG. 12 as the illustrated device is being used to exhale.

DESCRIPTION OF THE PREFERRED EMBODIMENTS

Figure 1:
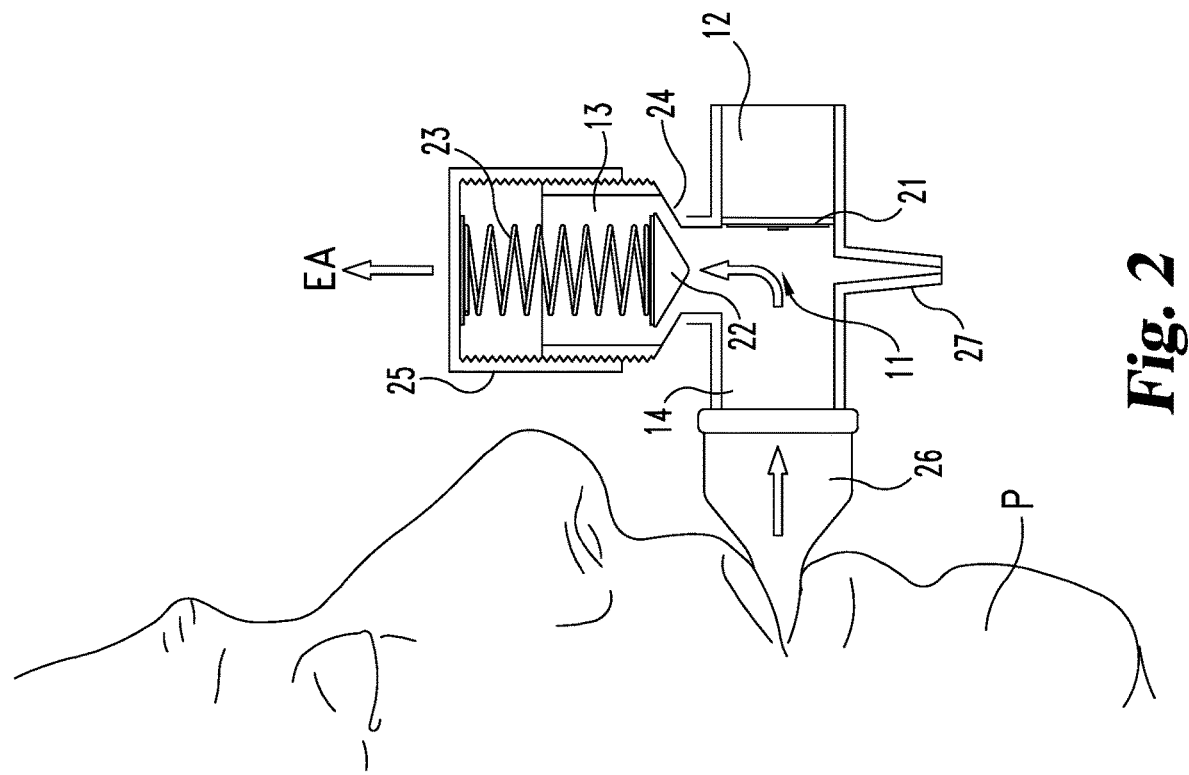
FIG. 1 shows a side view, in partial section, of one aspect of the present invention, particularly showing a device for increasing positive pressure within the patient's airways, as the illustrated device is being used to inhale.

For the purposes of promoting an understanding of the principles of the invention, reference will now be made to certain embodiments and specific language will be used to describe the same. It will nevertheless be understood that no limitation of the scope of the invention is thereby intended, with alterations and modifications being contemplated as would normally occur to persons skilled in the art to which the invention relates.

As indicated above, one aspect of the present invention relates to a device for providing resistance in an air pathway for a patient who is exhaling. In one embodiment the positive pressure airway device comprises:
 a) a central tube region;
 b) a first passageway for passing air into said central tube region when a patient breathing through the device inhales;
 c) a second passageway for passing air out of said central tube region when a patient breathing through the device exhales;
 d) a third passageway for passing air from said central tube region and into a patient when the patient breathing through the device inhales, and for passing air from said patient to said central tube when the patient breathing through the device exhales;
 e) a valve in the first passageway that allows air to flow in through the first passageway to the central tube when a patient using the device inhales, and that prevents air from flowing out through the first passageway when a patient using the device exhales;
 f) a valve in the second passageway that allows air to flow out from the second passageway when a patient using the device exhales with an expiratory air pressure greater than a selected pressure, that prevents air from flowing out through the second passageway when a patient exhales with an expiratory air pressure that is less than a selected air pressure, and that prevents air from flowing in through the second passageway when a patient using the device inhales,
wherein said valve in said second passageway includes:
 i) a stopper to close the passageway and prevent air from flowing through the passageway when the stopper is biased to its closed position, and
 ii) a stopper-biasing spring to maintain the stopper in a fixed and closed position unless the expiratory air pressure in the passageway is greater than a selected pressure;
wherein the volume available for expiratory air to occupy remains fixed and constant as long as the valves in the first and second passageways are closed, and
wherein said first passageway, said second passageway, and said third passageway are separate and distinct from each other.

In some embodiments the device has the general shape of an upside-down "T" with one of the two horizontal arms of the "T" being the first passageway for passing air into the central tube region when a patient breathing through the device inhales, the other horizontal arm being the third passageway for passing air from the central tube region and into a patient when the patient breathing through the device inhales and for passing air from the patient to the central tube when the patient breathing through the device exhales, and the vertical arm of the "T" being the second passageway for passing air out of the central tube region when a patient breathing through the device exhales.

In other embodiments the device has the general shape of a "+" with one of the two horizontal arms of the "+" being the first passageway for passing air into the central tube region when a patient breathing through the device inhales, and the other horizontal arm being the third passageway for passing air from the central tube region and into a patient when the patient breathing through the device inhales and for passing air from the patient to the central tube when the patient breathing through the device exhales. One of the verticals arm of the "+" is the second passageway for passing air out of the central tube region when a patient breathing through the device exhales, and the second vertical arm is a passageway for providing a flow of supplemental air to the central tube region while a first flow of air is entering the central tube region through the first passageway. The second (supplemental) flow of air may be separate and distinct from the first flow of air at least until the two flows intermix in the central tube region. The fourth passageway may be connected to auxiliary air and/or to a nebulizer for providing a drug to the patient when inhaling.

The passageways are preferably tube-shaped to facilitate air flow through the device. The tubes are preferably made of plastic, and have an inner diameter of between 0.50 inches and 1.5 inches, and more preferably between 0.75 inches and 1.25 inches.

The expiratory air passageway preferably includes a lower portion with an inner diameter of between about 10 mm and 20 mm, more preferably between about 12 mm and 16 mm, most preferably about 14 mm, and an upper portion with an inner diameter of between about 15 mm and 30 mm, more preferably between about 20 mm and 25 mm, most preferably about 22.5 mm. This allows the expiratory air passageway to have a sloped portion that is adapted to contact the plug or stopper used to close the passageway. In the most preferred embodiments the sloped portion has a tubular shape with a diameter that transitions smoothly from the diameter of the lower passageway portion to the diameter of the upper passageway portion. Accordingly, at the bottom of the sloped portion of the passageway the diameter is the same as the diameter of the lower passageway portion, and it is this diameter that the diameter of the stopper should exceed to allow the stopper to close the passageway. Similarly, at the top of the sloped portion of the passageway the diameter is the same as the diameter of the upper passageway portion, and it is this diameter that the diameter of the stopper should not exceed to allow free movement of the stopper in the passageway.

One or more of the passageways may be provided with surface features to cause air flow through the tube to be turbulent. Most preferably only the passageway for passing air out of the central tube region when a patient breathing through the device exhales provides turbulent air flow, and then only or primarily in the region where the air flows around the stopper.

In some embodiments the volume available for expiratory air to occupy remains fixed and constant as long as the valves in the first and second passageways are closed. Generally, that volume is defined by the volume of the central tube region, plus the volume of the third passageway, plus the volume of the first passageway between the central tube region and the valve in that passageway, plus the volume of the second passageway between the central tube region and the valve in that passageway. Accordingly, when a patient blows into the device the space available for expiratory air does not increase and the air resistance pressure faced by the patient increases until the pressure is sufficient to open the expiratory air valve.

In some embodiments the passageways are separate and distinct from each other.

In some embodiments the portion of the second passageway around the stopper is shaped or otherwise adapted to make air flow around the stopper turbulent.

Valves to control the flow of air are preferably included in at least the first and second passageways. As indicated above, the valve in the first passageway is preferably a valve that allows air to flow in through the first passageway to the central tube when a patient using the device inhales, and that prevents air from flowing out through the first passageway when a patient using the device exhales. A disc that bends away from a support to allow air to flow around the disc when blown from the direction of the support, yet is prevented from blowing away from the support and thus prevents air from flowing around the disc when blown toward the direction of the support, is one available option.

The valve in the second passageway is used adapted to allow air flow through the second passageway when a patient using the device exhales (i.e., when the patient is breathing out expiratory air (EA), while preventing air from through the second passageway when a patient using the device inhales (i.e., when the patient is breathing in inspiratory air (IA). In the preferred embodiments the valve provides a selectively-variable resistance to the air flow through the passageway.

In some embodiments the valve in the second/exhalation passageway comprises or consists essentially of a stopper to close the passageway and prevent air from flowing through the passageway when the stopper is biased to its closed position, and a stopper-biasing spring to bias the stopper to its closed position unless a pre-determined expiratory air pressure is provided in the passageway.

The stopper may comprise a seat portion that is sized and shaped to contact a portion of the expiratory air passageway so as to allow air flow through that passageway to be blocked. The seat portion is generally wider that the diameter of the lower expiratory air passageway so that the seat may contact the passageway wall and prevent air flow through the passageway. For expiratory air passageways having a lower portion sized between 10 mm and 20 mm, the seat will typically have a diameter of between 14 mm and 24 mm. For expiratory air passageways having a lower portion sized between 12 mm and 16 mm, the seat will typically have a diameter of between 16 mm and 20 mm. For expiratory air passageways having a lower portion sized at about 14 mm, the seat will typically have a diameter of about 18 mm.

The seat portion of the stopper may have a shape that corresponds to the portion of the passageway in which the stopper resides. This may allow the stopper to contact the passageway over an extended distance of at least 2 mm, and preferably at least 5 mm, and optionally between 2 mm and 10 mm.

In other embodiments the seat portion of the stopper may have a shape that does not correspond to the portion of the passageway in which the stopper resides. In this embodiment the stopper does not contact the passageway wall for an extended distance although some contact is necessary to allow the stopper to prevent air from flowing through the passageway.

In some embodiments the stopper is shaped or otherwise adapted to make air flow around the stopper turbulent. This may cause the forces acting on the stopper to be unbalanced as air flows around the stopper, causing the stopper to "flutter" and the pressure drop across the stopper to oscillate. The flutter motion may be an upward and downward motion of the valve plug, or it may be a side-to-side motion of the valve plug, or it may be both an upward and downward motion and a side-to-side motion of the valve plug.

The plug or stopper in the expiratory air passageway is preferably held against the passageway by a biasing spring. In other embodiments magnets or other structures may be used to apply a force against the valve stopper to move it toward the valve seat, and thus to aid in achieving correct Hz oscillation frequency as could otherwise be provided by a spring.

When used, the stopper-biasing spring is preferably a compression coil spring. The spring may be of a constant diameter or it may be tapered. When the spring has a constant diameter, the constant diameter may be a wide diameter that is greater than half of the diameter of the passageway in which the spring resides, or it may be a narrow diameter that is less than half, and optionally less than one-third, and alternatively optionally less than one-quarter, of the diameter of the passageway in which the spring resides. When the spring has a tapered diameter, the upper portion of the spring may have a wide diameter that is greater than half of the diameter of the passageway in which the spring resides, and the lower portion of the spring may have a narrow diameter that is less than half, and optionally less than one-third, and alternatively optionally less than one-quarter, of the diameter of the passageway in which the spring resides. As previously indicated, stopper-biasing spring may be attached at its first end to a spring housing, and at its second end to the stopper, with the center (interior) of the spring being free from any structure that would inhibit the "side-to-side" movement of the spring within the housing.

The stopper may be provided with a ridge or knob or other structure for optionally-releasable attachment of the stopper to a stopper-biasing spring.

In some embodiments the spring holding the stopper is shaped or positioned or otherwise adapted to cause the forces acting on the stopper to be unbalanced as air flows around the stopper, causing the stopper to "flutter" and the pressure drop across the stopper to oscillate.

In a further embodiment the device includes a spring-retaining housing to retain a stopper-biasing compression coil spring and to partially compress the spring to a length shorter than its free length. In certain preferred embodiments the spring-retaining housing is movable with respect to the stopper so that the spring-retaining housing is effective for varying the compression length of the spring, and thus for varying the expiratory air pressure/force needed to open the resistance valve.

As indicated above, the stopper and/or the spring and/or the expiratory air passageway may be adapted to provide unbalanced forces that cause the valve to "flutter" in response to a patient's exhalation air pressure. The flutter motion may be an upward and downward motion of the valve plug, or it may be a side-to-side motion of the valve plug, or it may involve both an upward and downward motion and a side-to-side motion of the valve plug. This fluttering motion of the valve plug may be caused, for example, by a stopper having a particular shape, and/or the use of a spring having a particular shape and/or connection with the stopper, and/or by having an air passageway with a shape and/or features that provide turbulent air flow. The turbulent or fluttering air flow provides advantages when compared with the more constant air flow provided by alternative designs. It is known that flutter or oscillation at certain frequencies (Hz) promote mucus secretion mobilization within the airways of the lungs.

The valve in the exhalation passageway preferably allows air to flow out through the device only when the patient exhales with an expiratory air pressure greater than 20 $cmH_2O$. In still other embodiments the device includes a valve in the exhalation passageway to allow air to flow out through the device only when the patient exhales with an expiratory air pressure greater than 30 $cmH_2O$. Preferably the force provided against the stopper by the spring is adjustable so that the expiratory air pressure needed to open the exhalation passageway may be varied and selected within the range of 10 $cmH_2O$ to 30 $cm/H_2O$.

In another embodiment of the present invention there is provided a method for requiring a patient to breathe out with a pre-determined expiratory air pressure. The method preferably comprises:
a) providing a device for providing resistance in an air pathway for a patient exhaling, the device comprising:
i) a central tube region;
ii) a first passageway for passing air into said central tube region when a patient breathing through the device inhales;
iii) a second passageway for passing air out of said central tube region when a patient breathing through the device exhales;
iv) a third passageway for passing air from said central tube region and into a patient when the patient breathing through the device inhales, and for passing air from said patient to said central tube when the patient breathing through the device exhales;
v) a valve in the first passageway that allows air to flow in through the first passageway to the central tube when a patient using the device inhales, and that prevents air from flowing out through the first passageway when a patient using the device exhales;
vi) a valve in the second passageway that allows air to flow out from the second passageway when a patient using the device exhales with an expiratory air pressure greater than a selected pressure, that prevents air from flowing out through the second passageway when a patient exhales with an expiratory air pressure that is less than a selected air pressure, and that prevents air from flowing in through the second passageway when a patient using the device inhales,
wherein said valve in said second passageway includes:
A) a stopper to close the passageway and prevent air from flowing through the passageway when the stopper is biased to its closed position, and
B) a stopper-biasing spring to maintain the stopper in a fixed and closed position unless the expiratory air pressure in the passageway is greater than a selected pressure;
wherein the volume available for expiratory air to occupy remains fixed and constant as long as the valves in the first and second passageways are closed, and
wherein said first passageway, said second passageway, and said third passageway are separate and distinct from each other; and
b) breathing out through said device with sufficient expiratory air pressure to cause said expiratory air valve to open, allowing air to exit the device.

In addition to the above the method may include the step of selecting a pre-determined expiratory air pressure and moving the spring housing with respect to the stopper so that the pressure necessary to move the topper to its open position is the pre-determined expiratory air pressure.

In some embodiments of the invention the method requires a pre-determined expiratory air pressure of between 10 $cmH_2O$ and 30 $cm/H_2O$. For example, some embodiments use a valve in the exhalation passageway that allows air to flow out through the device only when the patient exhales with an expiratory air pressure greater than 10 $cmH_2O$. In other embodiments the device uses a valve in the exhalation passageway that allows air to flow out through the device only when the patient exhales with an expiratory air pressure greater than 20 $cmH_2O$. In still other embodiments the device uses a valve in the exhalation passageway that allows air to flow out through the device only when the patient exhales with an expiratory air pressure greater than 30 $cmH_2O$.

It is to be appreciated that the present invention provides a device that is designed to increase positive pressure within the patient's airways during exhalation. This expands the lungs within patients that have compromised lungs due to decreased lung capacity resulting from COPD (Chronic Obstructive Pulmonary Disease), CHF (Congestive Heart Failure), Pulmonary Edema, decreased lung capacity due to pain or inhibited abdominal diaphragm function, and particularly atelectasis (the collapse of the Alveoli within the lungs). The use of the inventive positive pressure airway device (PPAD, optionally referred to as a pneumatic positive expiratory pressure device, or PPEPD) still requires physical effort from the patient, but decreases the amount of physical effort to achieve the desired alveoli expansion. This provides a therapy designed to decrease danger to the patient due to and during cardiopulmonary compromise listed above, and to prevent pulmonary complications due to compromised lung function.

Patients can do this with the positive pressure airway device in any situation. By increasing the pressure provided by the PPAD above 6 $cmH_2O$ in the alveoli, this pushes the blood from the Alveoli back into the pulmonary capillaries.

Higher pressures will achieve this in a faster manner. The PPAD is designed to function between 10 cmH$_2$O and 30 cmH$_2$O.

In some embodiments of the invention the device uses a valve in the exhalation passageway that prevents the patient from exhaling through the device unless the expiratory air pressure is at least 10 cmH$_2$O. In other embodiments the device includes a valve in the exhalation passageway to allow air to flow out through the device only when the patient exhales with an expiratory air pressure greater than 15 cmH$_2$O. In other embodiments the device includes a valve in the exhalation passageway to allow air to flow out through the device only when the patient exhales with an expiratory air pressure greater than 20 cmH$_2$O. In other embodiments the device includes a valve in the exhalation passageway to allow air to flow out through the device only when the patient exhales with an expiratory air pressure greater than 25 cmH$_2$O. In still other embodiments the device includes a valve in the exhalation passageway to allow air to flow out through the device only when the patient exhales with an expiratory air pressure greater than 30 cmH$_2$O. In yet other embodiments the device includes a valve in the exhalation passageway to allow air to flow out through the device only when the patient exhales with an expiratory air pressure greater than 35 cmH$_2$O. In still other embodiments the device includes a valve in the exhalation passageway to allow air to flow out through the device only when the patient exhales with an expiratory air pressure greater than 40 cmH$_2$O. More preferably, the device includes a valve that is variable with respect to the necessary expiratory air pressure so that the necessary expiratory air pressure may be selected to be essentially anywhere within the range of 10 cmH$_2$O to 40 cmH$_2$O, or most preferably within the range of 10 cmH$_2$O to 35 cmH$_2$O In use, the device is commonly used to provide up to about 1.5 liters per minute of air flow. However, it is to be appreciated that the device may also be used for flush-flow, in which substantially more (for example, 15 liters per minute or more) air (or other gas) may be passed through the device to prime the device.

As indicated above the inventive device may be adapted to provide unbalanced forces against the stopper plug. This may cause the plug to flutter and the pressure drop across the plug to oscillate. In particular, it is observed that while the pressure forces on the upstream face (inlet) of the disc are below the force applied by the spring (plus any backpressure forces downstream face/outlet of the disc), the valve is closed. When the inlet pressure forces become greater than the spring elastic forces, the valve opens. When the valve opens, flow begins through the device and results in a pressure drop across the valve. As the valve continues to open, the pressure drop across the valve rapidly decreases allowing flow to increase, the inlet pressure is reduced and the pressure forces on the upstream face (inlet) of the disc decrease below the force applied by the spring1 and the valve closes quickly. This cycle repeats at a designated frequency and pressure amplitude that is determined by the valve's geometry (valve shape or angles) which fixes the effective flow area, the effective force areas, and resulting valve flow characteristics (flow rate vs valve deflection).

The device can be attached to a continuous positive airway pressure (CPAP) mask to aid a patient in ventilation (blow off CO2) and oxygenate.

Figure 2:
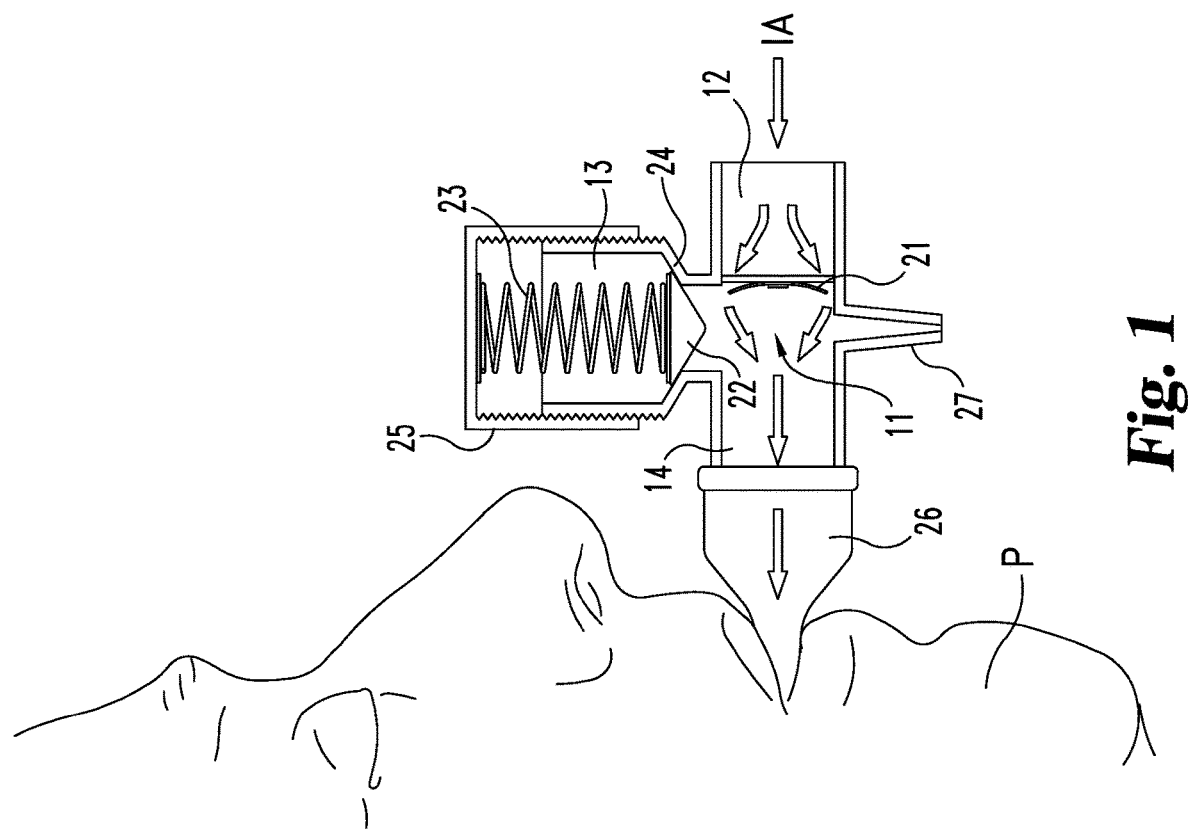
FIG. 2 shows a side view, in partial section, of one aspect of the present invention, particularly showing a device for increasing positive pressure within the patient's airways, as the illustrated device is being used to exhale.

Referring now to the drawings, FIGS. 1-2 show a side view of one embodiment of a positive pressure airway device, in partial section. The illustrated device includes a central tube portion 11 where a first passageway 12, a second passageway 13, and a third passageway 14 meet. First passageway 12 is the "inhalation" passageway through which inhalation air (IA) may enter the device when a patient using the device inhales. First passageway 12 may include an inhalation valve 21 that allows air to flow in through first passageway 12 to central tube portion 11 when a patient using the device inhales. Valve 21 may also prevent air from flowing out through first passageway 12 when a patient using the device exhales.

Second passageway 13 is the "exhalation" passageway through which expiratory air (EA) may leave the device when a patient using the device exhales. Second passageway 13 may include a variable-pressure exhalation valve 22 that allows air to flow out through second passageway 13 when a patient using the device exhales. Valve 22 may also prevent air from flowing in through second passageway 13 when a patient using the device inhales.

Third passageway 14 is the "patient breathing" passageway through which air passes into and out of the patient's lungs. Third passageway 14 receives air from first passageway 11 through central tube portion 11 when the patient inhales, and passes air out to second passageway 13 through central tube portion 11 when the patient exhales.

One or more valves may be used to control the air flow. As previously indicated, valve 21 may be used to allow air to flow in through first passageway 12 to central tube portion 11 when a patient using the device inhales. Valve 21 may also prevent air from flowing out through first passageway 12 when a patient using the device exhales. Similarly, valve 22 may allow air to flow out through second passageway 13 when a patient using the device exhales. Valve 22 may also prevent air from flowing in through second passageway 13 when a patient using the device inhales.

Valve 22 is preferably variable with respect to the pressure needed to open the valve. Most preferably valve 22 is biased closed with a pressure of between 10 cmH$_2$O and 30 cm/H$_2$O. The pressure needed to open the valve is selectable, so that when the patient selects an opening pressure of 10 cmH$_2$O to open the valve the valve will open when the patient exhales with an expiratory air pressure of at least 10 cmH$_2$O. Similarly, when the patient selects an opening pressure of 30 cmH$_2$O to open the valve the valve will open when the patient exhales with an expiratory air pressure of at least 30 cmH$_2$O.

Accordingly, it can be seen in FIG. 1 that valve 21 opens when the patient P inhales through the device, and it can be seen in FIG. 2 that valve 21 closes on exhalation. Similarly, it can be seen in FIG. 1 that valve 22 remains biased closed when the patient inhales through the device, and it an be seen in FIG. 2 that valve 22 opens when the expiratory air pressure exceeds the selected spring pressure. This combination of valves forces the patient's air to exit through the expiratory pressure exhaust port by forcing the expiratory pressure valve to push open against the pressure control spring. A mouthpiece 26 may be used by patient P.

To further illustrate the operation of valve 22, the valve may comprise a stopper 22 that seats in a lower, sloped portion 101 of exhalation tube 24 in passageway 13. Spring 23 biases stopper 22 downward with a pressure equal to the expiratory air pressure that is desired. As previously indicated, valve 22 (or any stopper for oscillation) and seat the lower, sloped portion 101 of exhalation tube 24 may contain magnets to aid in achieving a correct Hz oscillation frequency.

The pressure exerted by spring 23 may be variable. For example, a spring-retaining housing 25 may be used to vary the compression applied to spring 23, and thereby to vary the pressure needed to move stopper 22 to its open position. Threaded outer sidewalls on exhalation tube 24 may cooperate with threaded inner sidewalls of spring-retaining housing 25 to vary the length of passageway 13, and thus the pressure exerted by spring 23.

FIG. 3 shows an exploded section view of the device of FIGS. 1 and 2. Spring 23 is positioned above stopper 22 and presses down on stopper 22 when spring-retaining housing 25 is screwed onto tube 24. Cap 28 retains spring 23 in place in passageway 13.

FIG. 4 shows an end view the device of FIGS. 1 and 2, showing the opening of the inhalation tube and the valve support 31 therein.

FIG. 5 shows a top plan view the device of FIGS. 1 and 2, showing the opening of the exhalation tube and the spring-retaining housing 25 thereon. Spring-retaining housing 25 includes openings 29 to allow expiratory air to exit the device, and retaining arms 32 to retain the spring in the housing.

FIG. 6 shows a side view the device of FIGS. 1 and 2, with a nebulizer 30 attached to the inhalation opening.

Figure 7:
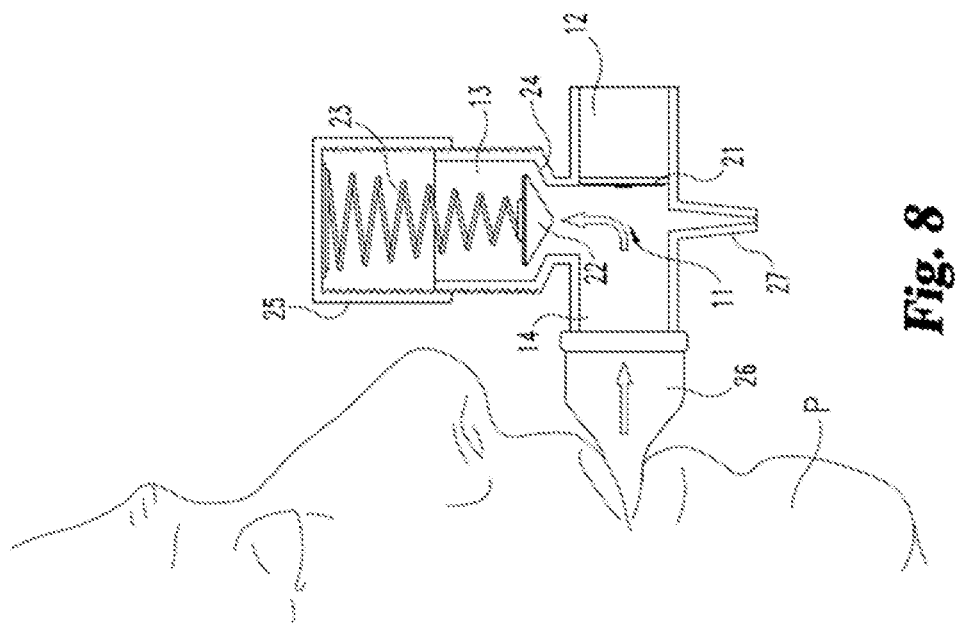
FIG. 7 shows a side view, in partial section, of the device of FIGS. 1 and 2 with the spring-retaining housing being in its compressed position.

FIG. 7 shows a side view, in partial section, of the device of FIGS. 1 and 2 with the spring-retaining housing being in its compressed position. In the compressed position, spring-retaining housing 25 has been moved downward over second passage 13 by screwing the threaded housing toward the bottom of the passageway. In the illustrated condition the patient is inhaling and air is entering the device as stopper 22 remains seated to seal exhalation tube 24 closed.

Figure 8:
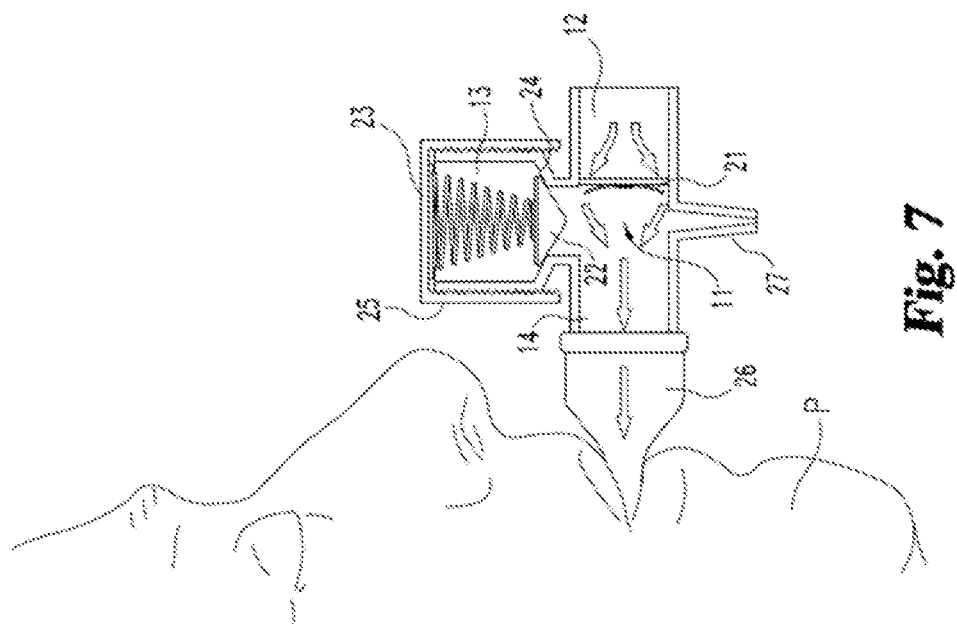
FIG. 8 shows a side view, in partial section, of the device of FIGS. 1 and 2 with the spring-retaining housing being in its relaxed position.

FIG. 8 shows a side view, in partial section, of the device of FIGS. 1 and 2 with the spring-retaining housing being in its relaxed position. In the relaxed position, spring-retaining housing 25 has been moved upward away from the lower portion of second passage 13 by screwing the threaded housing away from the bottom of the passageway. In the illustrated condition the patient is exhaling and air is leaving the device as stopper 22 is pushed upward by an expiratory air pressure that exceeds the downward pressure provided by spring 23.

Figure 9:
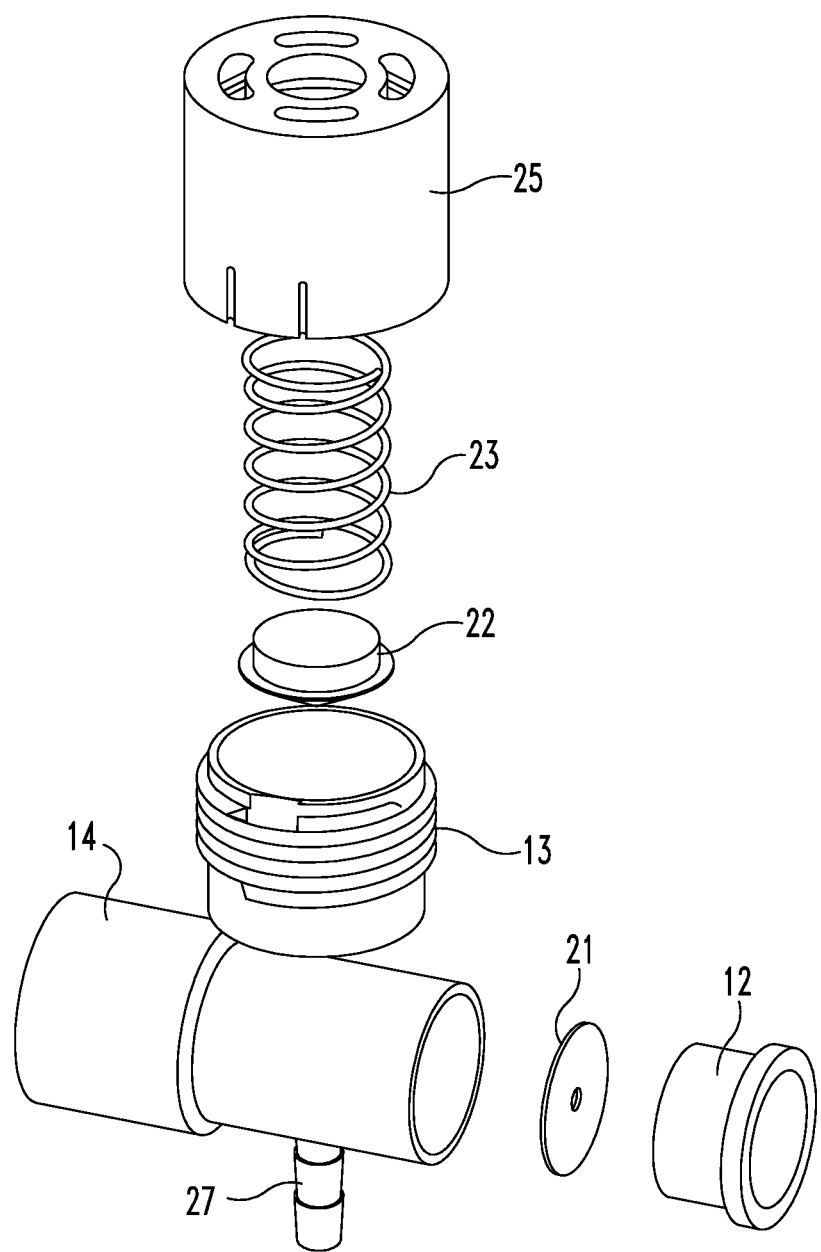
FIG. 9 shows an exploded view of the device of FIGS. 1 and 2.

FIG. 9 shows an exploded view of the device of FIGS. 1 and 2.

Figure 10:
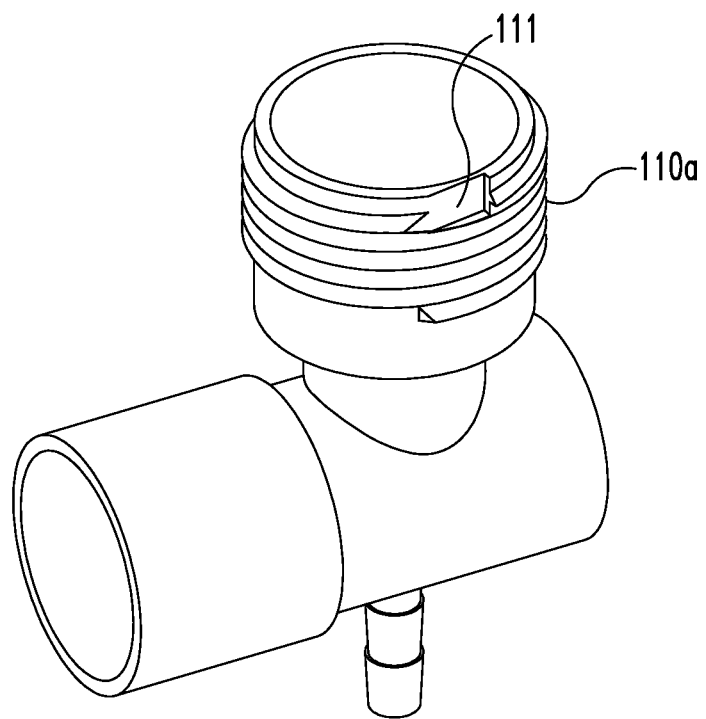
FIG. 10 shows a perspective view of the exhaust/exhalation tube of one aspect of the present invention, showing the threaded outer wall.

FIG. 10 shows a perspective view of the exhaust/exhalation tube of one aspect of the present invention, showing the threaded outer wall. Threads 110 may include a cut-out 111 to receive a ramp 112. Ramp 112 and cut-out 111 comprise a ramp-lock to lock housing 25 onto tube 24 and prevent the housing from being removed from the tube unless the ramp-lock is released.

Figure 11:
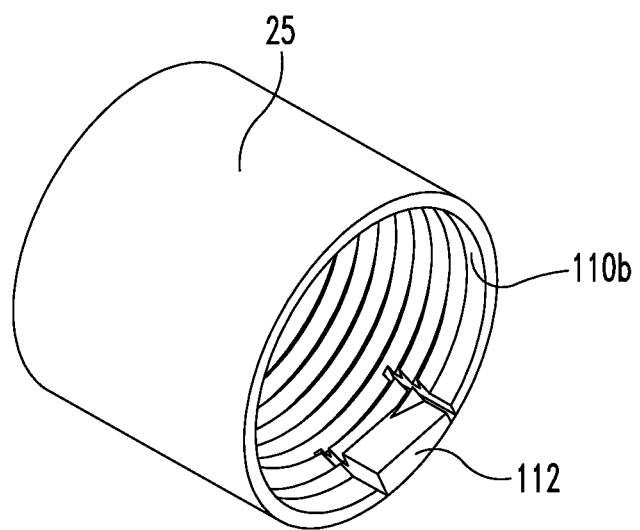
FIG. 11 shows a perspective view of the spring-retaining housing of one aspect of the present invention, showing the threaded inner wall.
Figure 14:
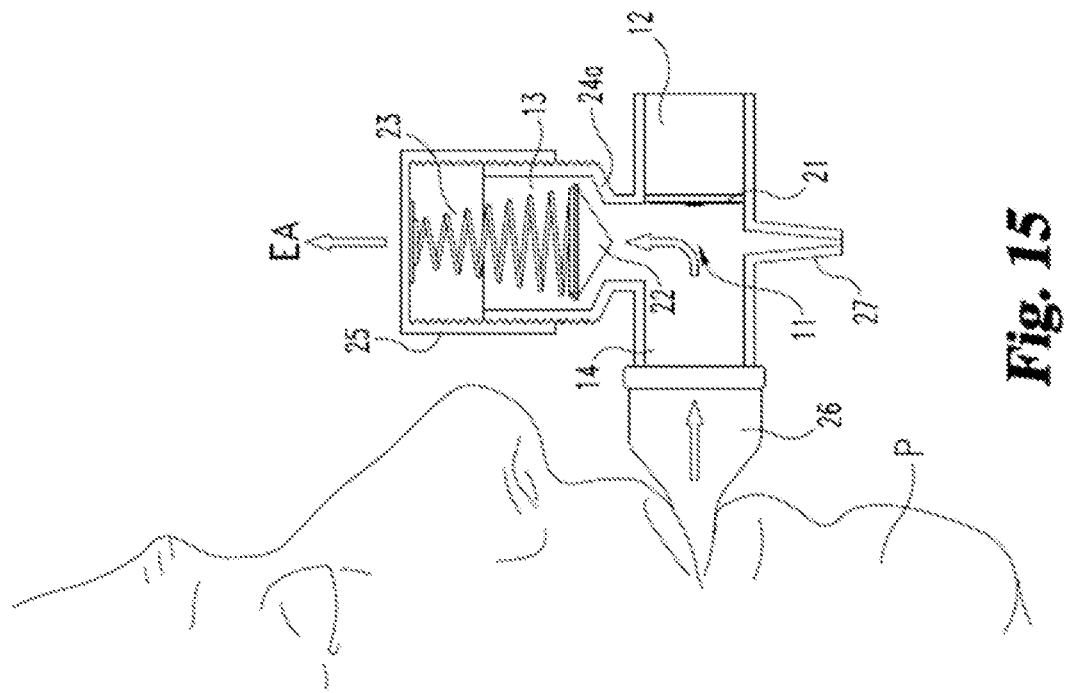
FIGS. 14 and 15 show a side view, in partial section, of the device of FIG. 12 as the valve is fluttering from left to right while the device is being used to exhale.
Figure 15:
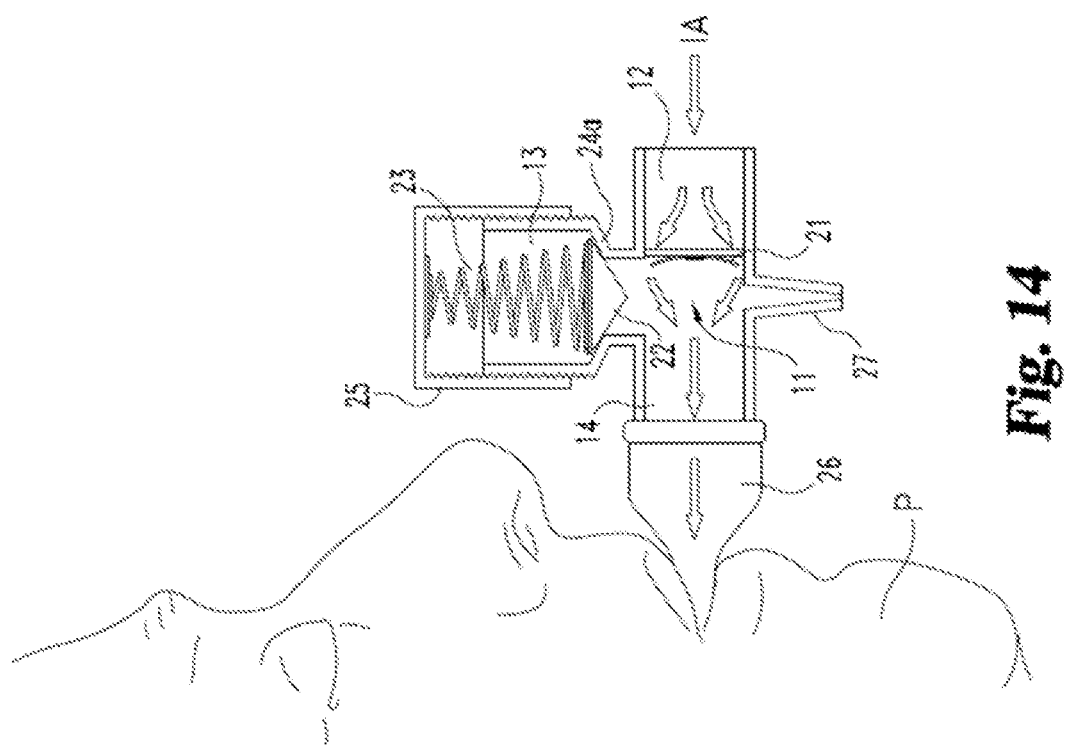

FIG. 11 shows a perspective view of the spring-retaining housing of one aspect of the present invention, showing the threaded inner wall. A ramp 112 may be included to lock the housing 25 onto tube 24 unless the user releases the ramp-lock assembly.

As shown in several Figures, an $O_2$ nipple adapter 27 may be used to facilitate the supply of supplemental oxygen (or other gas) to the patient if and when needed. The nipple adaptor allows supplemental gas to be provided to the patient at any range from less than 1 liter per minute to at least about 15 liters per minute. This is particularly useful for providing the flush flow technique that may be used to prime the device.

It can be seen from the foregoing Figures that valve 21 may include a diaphragm that is deflected inward to allow air to enter during inhalation. When exhaling, that diaphragm presses against support 31 to prevent air from exiting through that opening. Instead, air is forced to exit through the exhalation control valve which provides a positive airway pressure against the patient. When the patient blows with sufficient force, the biasing force of the pressure control spring is overcome and air may exit through the exhalation ports. The positive airway pressure may be controlled within limits by using the pressure control knob to shorten or lengthen the space in the upper housing, thus increasing or decreasing the pressure provided by the spring.

It can be seen from the above that the present invention allows the patient to both inhale and exhale through the device. The device may therefore be used as for normal breathing, without manipulating the device in any way and without requiring the patient to put the device aside to inhale.

It can also be seen from the above that various benefits may be provided by one or more of the various disclosed embodiments. For example, a patient may achieve positive pressure exhalation without compromising expiratory air flow. This provides the benefit of requiring less work by the patient for breathing by (APPE) active positive pressure exhalation. Exhalation is normally passive.

It is known to the art that about two-thirds to three-quarters of a patient's breathing time is spent in exhalation with normal lung function. The inventive PPAD uses exhalation to advantage with positive pressure exhalation. This also creates a normal I/E ratio when the patient is in distress preventing hyperventilation.

The PPAD may be used for expiratory positive pressure ventilation (EPPV) or positive exhalation pressure (PEP). The device is designed to relieve difficulty of breathing at onset of respiratory distress by means of APPE or FPPE (forced positive pressure exhalation) with asthma attacks. This is comparable to the function of PEP with a broader explanation of uses of EPPV or PEP.

The PPAD may also be used for simple lung expansion exercises for patients who have compromised lung function due to restriction and or pain from thoracic and abdominal surgeries.

The PPAD may be used for early intervention of patients who are pending respiratory distress. These patients can benefit greatly from EPPV to prevent or recover from respiratory distress in a short period of time.

The PPAD may prevent air trapping by splinting the bronchiole tubes during APPE.

The PPAD may allow for better ventilation and oxygenation, and may act as an internal splint in the smaller bronchiole walls and alveoli to prevent respiratory distress with pulmonary edema resulting from atelectasis and/or CHF causing tremendous negative pressures within the airways. Respiratory distress may be minimized by recruiting and hyper inflating alveoli during APPE. Similarly, the PPAD may help patients expand hypo inflated lungs due to lack of proper deep breathing.

The PPAD may help hold the normal shape of alveoli during exhalation with patients who suffer from obstructive lung disease by splinting the flaccid air sacs and damaged bronchiole tubes. The result may be less stagnant lungs which will help mobilize secretions (increased expansion and contraction of the lungs).

The PPAD may achieve desired pressure without compromising flow. The result may be less energy expended during device use resulting in greater chances of recovery.

In some embodiments the PPAD may be adapted so as to be used with supplemental oxygen or an aerosol nebulizer if desired by patient or medical personnel.

FIGS. 12-15 show a side view, in partial section, of an alternative embodiment of one aspect of the present invention, particularly showing a device similar to the device shown in FIGS. 1 and 2, but with a tapered spring and a rounded valve seat. In FIG. 12 the device is being used to inhale, and in FIGS. 13-15 the device is being used to exhale. This causes the valve to flutter from side-to-side when the patient exhales and may provide turbulent air flow when compared to the more constant air flow provided by the embodiment of FIGS. 1 and 2, and may advantageously be used to provide an oscillating pressure during exhalation.

Figure 16:
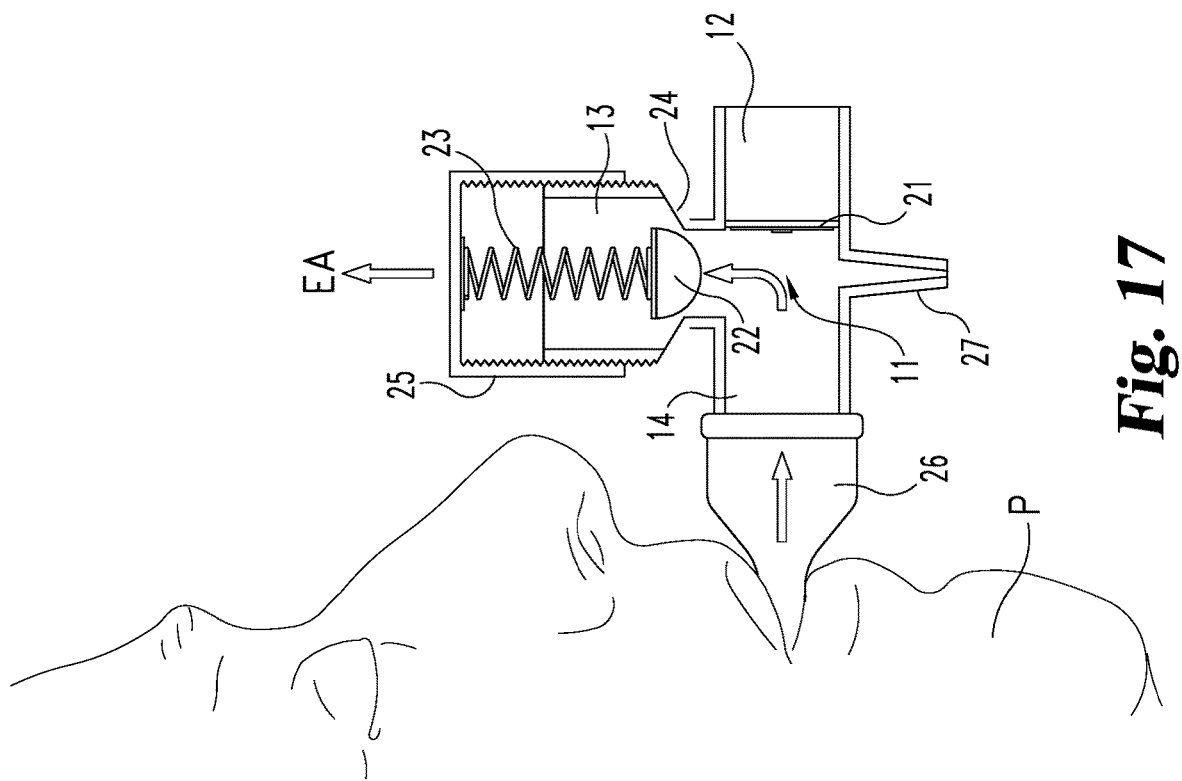
FIG. 16 shows a side view, in partial section, of one aspect of the present invention, particularly showing a device according to FIG. 1 but with a narrow spring and a rounded valve seat, as the illustrated device is being used to inhale.
Figure 17:
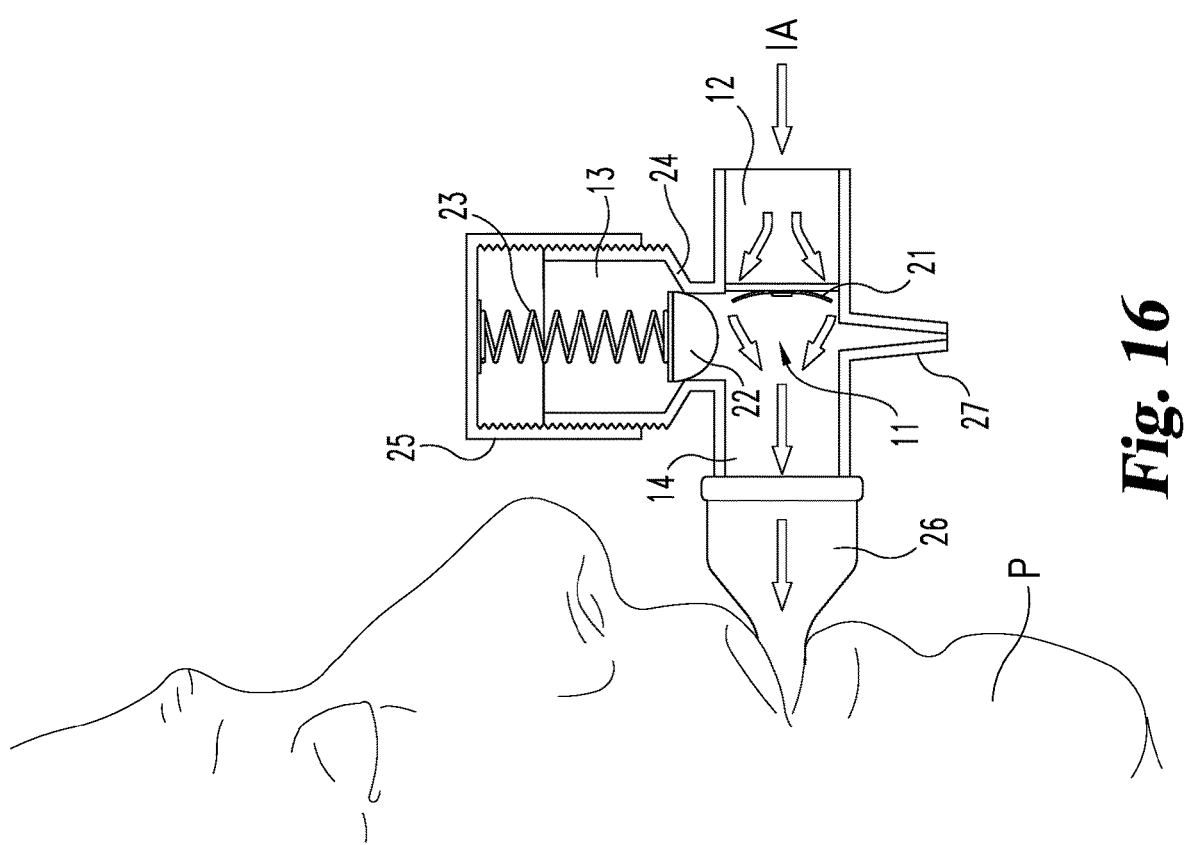
FIG. 17 shows the device of FIG. 16 as the device is being used to exhale.
Figure 19:
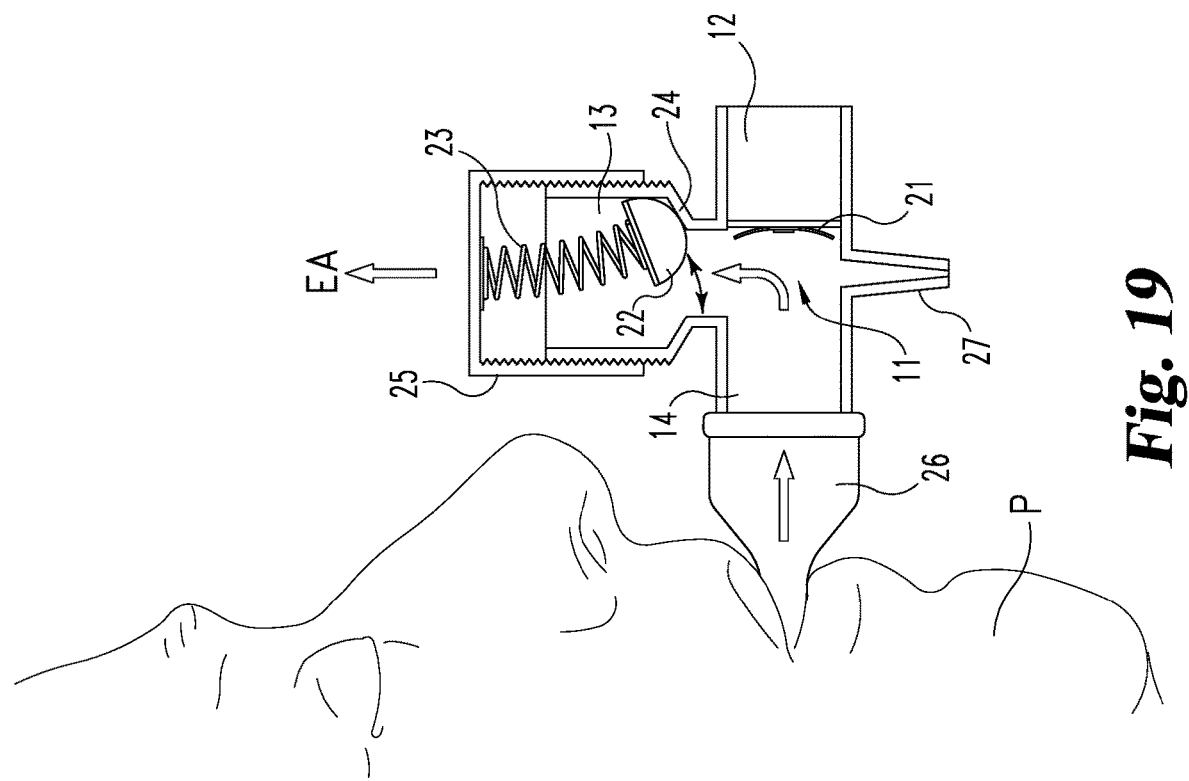
FIGS. 18 and 19 show a side view, in partial section, of the device of FIG. 16 as the valve is fluttering from left to right while the device is being used to exhale.
Figure 18:
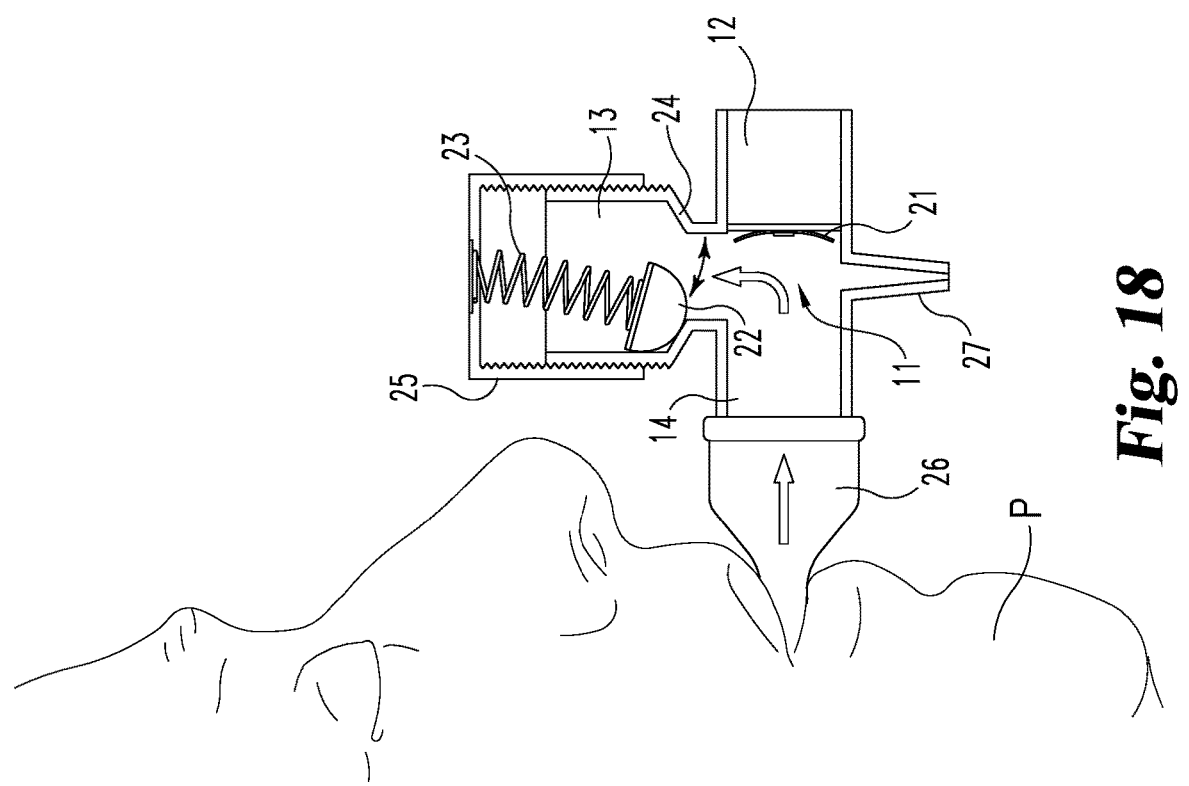

FIGS. 16-19 show a side view, in partial section, of an alternative embodiment of one aspect of the present invention, particularly showing a device similar to the device shown in FIGS. 1 and 2, but with a thin, narrow spring and a rounded valve seat. In FIG. 16 the device is being used to exhale, and in FIGS. 17-19 the device is being used to exhale.

Figure 20:
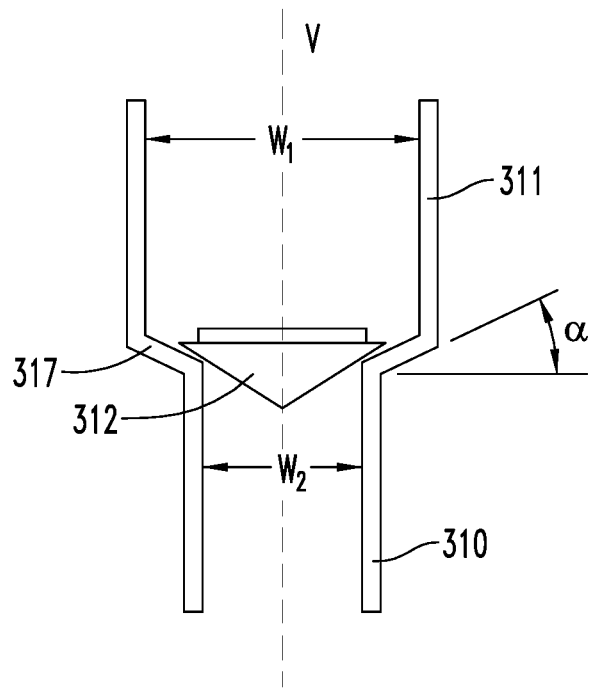
FIG. 20 shows one embodiment of a valve in an exhalation passageway, according to one embodiment, illustrating the angle α formed by the transitional portion of the passageway.

FIG. 20 shows one embodiment of an exhalation passageway with an exhalation valve positioned therein, according to one embodiment. The passageway has a lower portion defined by lower wall 310, and an upper portion defined by upper wall 311. The lower portion defined by wall 310 has a passageway diameter $W_2$ that is smaller than the passageway diameter $W_1$ of the upper portion defined by wall 311. A transitional/slanted area 317 connects lower wall 310 to upper wall 311. Transitional area 317 between the lower and upper portions is slanted at an angle with respect to a line perpendicular to the vertical axis "V" of the passageway, thus defining a valve seat angle $\alpha$ in the passageway. Expiratory valve plug 312 is positioned in the passageway such that a portion of the plug contacts the slanted transitional sloped wall, thus closing the passageway when the plug is biased against and contacts the wall.

Figure 21:
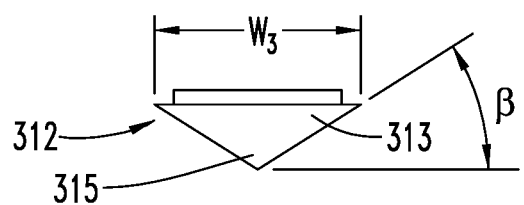
FIG. 21 shows a plug/stopper that may be used in preferred embodiments of the present invention, showing the angle β that is defined by the plug/stopper surface.

FIG. 21 shows one embodiment of a plug or stopper that may be used in the valve in an exhalation passageway. Plug/stopper 312 has a width $W_3$ that is larger than passageway diameter $W_2$ but smaller than the passageway diameter $W_1$. As indicated above, this allows the outer portion 313 of the plug/stopper to contact the slanted/sloped transitional wall 317, thus closing the passageway when the stopper is biased against and contacts that wall, yet allows air to flow around the plug when the stopper is raised from and does not contact slanted/sloped transitional wall 317. The outer portion of plug/stopper 312 has a slanted/sloped contact area 313 that adopts an angle $\beta$ with respect to a line perpendicular to the vertical axis of the plug (i.e., angle $\beta$ is the angle between the plug surface and a line perpendicular to the vertical axis of the passageway when the plug is pushed to its closed position). Plug/stopper surface angle $\beta$ (optionally referred to as valve angle $\beta$) may or may not be the same as valve seat angle $\alpha$. The lower portion 315 of plug/stopper 312 extends into lower passageway portion 310, and has a symmetrical shape to provide a desirable air flow around the plug when the plug does not contact the passageway wall.

Figure 22:
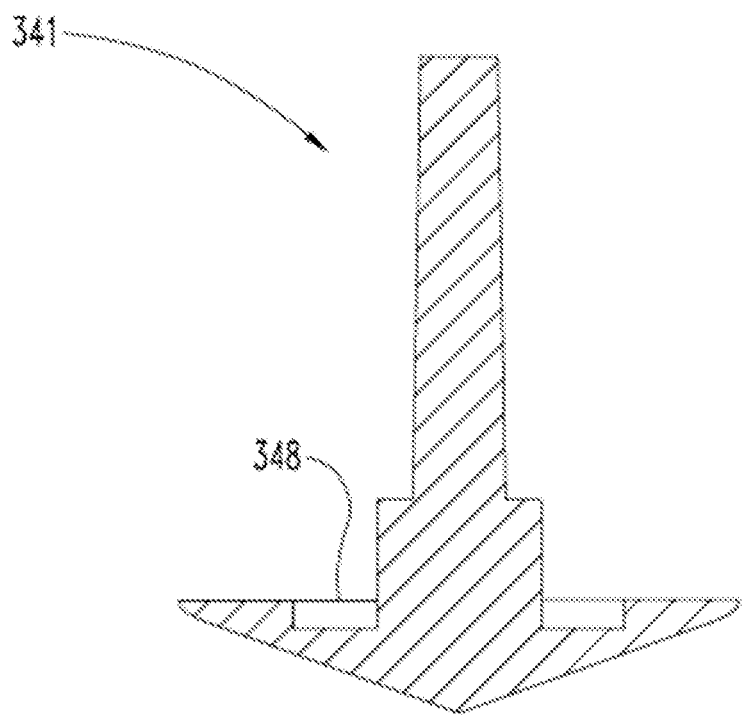
FIG. 22 shows one embodiment of a valve effective for use in an exhalation passageway, according to one embodiment.

FIG. 22 shows another embodiment of a plug that may be used in the valve in an exhalation passageway. Plug 341 has a width that is larger than passageway diameter $W_2$ but smaller than the passageway diameter $W_1$ to allow the bottom of the plug to contact slanted/sloped transitional wall 317 when the plug is biased against that wall, and to allow air to flow around the plug when the plug is raised from and does not contact slanted/sloped transitional wall 317. The bottom portion of plug 341 has a slanted/sloped contact area that adopts an angle $\beta$ that may or may not be the same as passageway wall angle $\alpha$. The lower portion of plug 341 extends into lower passageway portion 310, and has a symmetrical shape to provide a desirable air flow around the plug when the plug does not contact the passageway wall.

The stopper of FIG. 22 may include a space 348 for a weight. In the illustrated embodiment the stopper is made of a first material having a first weight per unit volume. Space 348 for a weight may be filled with a second material having a weight per unit volume that is greater than said first weight per unit volume. For example, the main body of the stopper may be made of acrylonitrile butadiene styrene (ABS), and the weight may be made of stainless steel. As can be seen from the illustration, the weighted portion may be positioned below the region at which the stopper contacts the second passageway when sealing the second passageway from air flow.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. In addition, it is to be appreciated that the present invention may comprise or consist essentially of any or all of the illustrated or described embodiments, devices, and/or features. For example, the present invention includes devices comprising each of the embodiments and/or features illustrated in FIGS. 1 through 22, and the present invention includes devices consisting essentially of any of the embodiments and/or features illustrated in FIGS. 1 through 22.

The invention claimed is:

1. A device for providing resistance in an air pathway for a patient who is exhaling, the device comprising:
   a) a central tube region;
   b) a first passageway for passing air into the central tube region when the patient breathing through the device inhales;
   c) a second passageway for passing air out of the central tube region when the patient breathing through the device exhales, wherein the second passageway has an upper portion defined by an upper wall, a lower portion defined by a lower wall, and a transitional wall connecting the lower wall to the upper wall, and wherein the transitional wall is slanted at an angle $\alpha$ with respect to a line perpendicular to the vertical axis of the second passageway, thus providing a passageway having a valve seat angle $\alpha$;
   d) a third passageway for passing air from the central tube region and into the patient when the patient breathing through the device inhales, and for passing air from the patient to the central tube when the patient breathing through the device exhales;
   e) a valve in the first passageway that allows air to flow in through the first passageway to the central tube when the patient using the device inhales, and that prevents air from flowing out through the first passageway when the patient using the device exhales;
   f) a valve in the second passageway that allows air to flow out from the second passageway when the patient using the device exhales with an expiratory air pressure greater than a selected pressure, that prevents air from flowing out through the second passageway when the patient exhales with an expiratory air pressure that is less than said selected pressure, and that prevents air from flowing in through the second passageway when the patient using the device inhales, wherein the valve in said second passageway includes:
      i) a stopper to close the second passageway and to prevent air from flowing through the second passageway when the stopper is biased to a closed position, and ii) a stopper-biasing spring to maintain the stopper in its closed position unless the expiratory air pressure in the second passageway is greater than the selected pressure, wherein the stopper-biasing spring is a coil spring having a stopper end connected to the stopper, a cap end opposite the stopper end, and an interior; and g) a spring housing cap connected to the cap end of the stopper-biasing spring and effective to retain the stopper-biasing spring and to partially compress the spring to a length shorter than its free length, wherein the spring housing cap is movable with respect to the transitional wall of the second passageway so that movement of the spring housing cap is effective for varying the compression length of the spring, and thus is effective for varying the expiratory air pressure that will cause the valve of the second passageway to open, and wherein the stopper-biasing spring is attached at its first end to the spring housing cap, and at its second end to the stopper, with the spring interior being free from any structure that would inhibit "side-to-side" movement of the spring within the second passageway;

wherein the stopper has an exterior surface defining a stopper angle β with respect to a line perpendicular to the vertical axis of the stopper.

2. A device according to claim 1 wherein the valve seat angle α is greater than the stopper angle β.

3. A device according to claim 2 wherein said valve seat angle α is between 20° and 30° and said stopper angle β is between 15° and 25°.

4. A device according to claim 3 wherein said valve seat angle α is approximately 25° and said stopper angle β approximately 20°.

5. A device according to claim 4 wherein said stopper is made of a first material having a first weight per unit volume, and includes a weighted portion made of a second material having a weight per unit volume that is greater than said first weight per unit volume.

6. A device according to claim 5 wherein the weighted portion is positioned below a region at which the stopper contacts the second passageway when sealing the second passageway from air flow.

7. A device according to claim 1 wherein the valve seat angle α is less than or equal to the stopper angle β.

8. A device according to claim 1 wherein said spring housing cap is movable with respect to the stopper so that movement of the spring housing cap is effective for varying expiratory air pressure at least within the range of 10 cm H2O to 25 cm H2O.

9. A device according to claim 1 and further including a fourth passageway for providing a flow of supplemental air to said central tube region while a first flow of air is entering the central tube region through the first passageway, wherein the supplemental flow of air is separate and distinct from the first flow of air at least until the two flows intermix in the central tube region.

10. A device according to claim 1 wherein the volume available for expiratory air to occupy remains fixed and constant as long as the valves in the first and second passageways are closed.

11. A device according to claim 1 wherein the stopper-biasing spring tapers inward from its cap end to its stopper end.

12. A device according to claim 1 wherein the stopper-biasing spring tapers outward from its cap end to its stopper end.

13. A device according to claim 1 wherein the valve seat angle α is greater than the stopper angle β, and the stopper-biasing spring tapers inward from its cap end to its stopper end.

14. A device according to claim 1 wherein the valve seat angle α is less than the stopper angle β, and the stopper-biasing spring tapers outward from its cap end to its stopper end.

15. A method for allowing a patient to breathe out only with a pressure at least as great as a selected pressure, said method comprising:

a) providing a device for providing resistance in an air pathway for the patient exhaling, the device comprising:

1) a central tube region;

2) a first passageway for passing air into the central tube region when the patient breathing through the device inhales;

3) a second passageway for passing air out of the central tube region when the patient breathing through the device exhales, wherein the second passageway has an upper portion defined by an upper wall, a lower portion defined by a lower wall, and a transitional wall connecting the lower wall to the upper wall, and wherein the transitional wall is slanted at an angle α with respect to a line perpendicular to the vertical axis of the second passageway, thus providing a second passageway having a valve seat angle of the angle α;

4) a third passageway for passing air from the central tube region and into the patient when the patient breathing through the device inhales, and for passing air from the patient to the central tube when the patient breathing through the device exhales;

5) a valve in the first passageway that allows air to flow in through the first passageway to the central tube when the patient using the device inhales, and that prevents air from flowing out through the first passageway when the patient using the device exhales;

6) a valve in the second passageway that allows air to flow out from the second passageway when the patient using the device exhales with an expiratory air pressure greater than the selected pressure, but that prevents air from flowing out through the second passageway when the patient exhales with an expiratory air pressure that is less than said selected air pressure, and that prevents air from flowing in through the second passageway when the patient using the device inhales, wherein the valve in said second passageway includes:

i) a stopper to close the second passageway and to prevent air from flowing through the second passageway when the stopper is biased to a closed position, and ii) a stopper-biasing spring to maintain the stopper in its closed position unless the expiratory air pressure in the second passageway is greater than the selected pressure, wherein the stopper-biasing spring is a coil spring having a first end connected to the stopper, a second end opposite the first end, and an interior; and 7) a spring housing cap connected to the second end of the stopper-biasing spring and effective to retain the stopper-biasing spring and to partially compress the spring to a length shorter than its free length, wherein the spring housing cap is movable with respect to the transitional wall of the second passageway so that movement of the spring housing cap is effective for varying the compression length of the spring, and thus is effective for varying the expiratory air pressure that will cause the valve of the second passageway to open, and wherein the stopper-biasing spring is attached at its first end to the spring housing cap, and at its second end to the stopper, with the spring interior being free from any structure that would inhibit "side-to-side" movement of the spring within the second passageway;
wherein the stopper has an exterior surface defining a stopper angle $\beta$ with respect to a line perpendicular to the vertical axis of the stopper; and b) breathing out through said device with sufficient expiratory air pressure to cause the valve of the second passageway to open, allowing air to exit the device.

* * * * *